(12) United States Patent
Diekhans et al.

(10) Patent No.: US 6,389,884 B1
(45) Date of Patent: *May 21, 2002

(54) DEVICE AND METHOD FOR MEASURING THE MOISTURE OF CROP MATERIAL IN AGRICULTURAL MACHINES

(75) Inventors: Norbert Diekhans, Gütersloh; Alfons Kersting, Oelde-Lette; Willi Behnke, Steinhagen, all of (DE)

(73) Assignee: CLAAS Selbstfahrende Erntemaschinen GmbH, Harsewinkel (DE)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/168,533

(22) Filed: Oct. 8, 1998

(51) Int. Cl.⁷ .......................... G01N 5/02; A01F 21/00; A01D 75/28
(52) U.S. Cl. ........................... 73/73; 460/7; 56/10.2 B; 56/10.2 R
(58) Field of Search ............................ 73/73; 56/10.2 B, 56/10.2 R; 460/7

(56) References Cited

U.S. PATENT DOCUMENTS

| | | | |
|---|---|---|---|
| 4,527,241 A | * 7/1985 | Sheehan et al. .............. 701/50 |
| 5,106,339 A | * 4/1992 | Braun et al. .................... 460/7 |
| 5,327,708 A | * 7/1994 | Gerrish ..................... 56/10.2 R |
| 5,514,973 A | * 5/1996 | Byler et al. ...................... 73/73 |
| 5,586,033 A | * 12/1996 | Hall ............................ 701/50 |
| 5,616,851 A | 4/1997 | McMahon et al. |
| 5,716,272 A | * 2/1998 | Nelson ........................... 460/7 |
| 5,871,397 A | * 2/1999 | Nelson et al. .................. 460/7 |
| 5,957,773 A | * 9/1999 | Olmsted et al. ................ 460/7 |
| 6,121,782 A | * 9/2000 | Adams et al. ............... 324/689 |
| 6,150,617 A | * 11/2000 | Hart et al. ................ 177/25.13 |

FOREIGN PATENT DOCUMENTS

| | | | |
|---|---|---|---|
| DE | 33 06 460 A1 | 8/1984 | ......... G01N/27/04 |
| DE | 358 00 839 C2 | 7/1986 | ......... G01N/27/22 |
| DE | 41 05 851 A1 | 8/1992 | ............. G01F/1/86 |
| DE | 692 09 898 T2 | 12/1992 | ......... G01N/33/10 |
| DE | 196 48 126 A1 | 5/1998 | ......... A01D/43/08 |

* cited by examiner

*Primary Examiner*—Hezron Williams
*Assistant Examiner*—Michael Cygan
(74) *Attorney, Agent, or Firm*—Husch & Eppenberger, LLC; Robert E. Muir

(57) ABSTRACT

The invention relates to a moisture measuring device and a method for measuring moisture of the crop material in harvesting machines. To improve the moisture measurement, the combination of the moisture measuring device with a sensor state monitoring device ensures that the manual calibration effort is reduced. According to the method disclosed in the present invention, the correction value from the measured moisture value is at least, in part, a function of the working condition of the harvesting machine.

15 Claims, 1 Drawing Sheet

DEVICE AND METHOD FOR MEASURING THE MOISTURE OF CROP MATERIAL IN AGRICULTURAL MACHINES

BACKGROUND OF THE INVENTION

The present invention relates generally to agricultural machinery and, more particularly, to improvements in measuring moisture in crops. The invention provides a moisture measuring device as well as a method for measuring moisture of the crop material in harvesting machines.

It is known in the art that moisture sensors can be used in agricultural machines to precisely measure the quantity of harvested grain, especially corn, based upon a measurement of the harvested crop material moisture. For example German Patent Application DE 41 05 857 provides a moisture measuring device which uses a bypass system to continuously determine the moisture of the harvested crop material. Furthermore, U.S. Pat. No. 5,616,851 discloses a moisture sensor which operates by accumulating a quantity of material to be measured in a measuring chamber, then performing the measurement and returning the measured material to the stream of crop material prior to beginning a new measuring cycle. Arranging continuously operating moisture sensors directly in the path of conveying the crop material has also been attempted. For example, a moisture sensor has been arranged in a grain tank filling screw, instead of a spiral, or in the grain tank. These locations for mounting the sensors were selected to be independent of the throughput of crop material because throughput fluctuations affect the accuracy of the moisture measurement. However, because a sensor in the filling screw interferes with the conveying of material and a sensor in the grain tank always allows only one measurement per grain tank, both systems were commercially unsuccessful.

A microwave sensor which is constructed as a smooth sensor and is capable of determining, by use of microwaves, the moisture content of the crop material moving past the smooth sensor is known in the art from German Patent Application DE 196 48 126. The microwave sensor disclosed is relatively expensive and is also structurally elaborate, as the environment must be shielded from the microwaves.

All moisture sensors known from the state of the art must be calibrated to obtain accurate moisture values. There is a distinction between calibration related to the material to be measured, which depends upon the type of crop material, and calibration related to processing, which is determined by the density of the material to be measured, the quantity of material conveyed and the conveying members. For calibration related to the material to be measured, there are provided calibrating curves which can be accessed by the user of the moisture measuring device. These curves are in each case valid for certain temperatures of material. However, the need for processing-related calibration is, in practice, bypassed by setting up measuring points with at least temporarily constant measurement conditions. These measuring points do not always ensure constant measurement conditions. Therefore, errors arise, which multiply if further processing-related error sources of measurements, such as fouling of the sensor, are ignored. Under such conditions, the accuracy of the moisture value depends on the harvesting machine operator's care and understanding for the concerns of the moisture measuring device, which cannot always be presupposed.

It is an object of the present invention to provide an improved moisture measuring device which minimizes the above described drawbacks of state of the art moisture measuring devices.

SUMMARY OF THE INVENTION

In accordance with the present invention there is provided an agricultural machine including a moisture measuring device having a moisture sensor for measuring moisture of the crop material in the machine, and a sensor state monitoring device interconnected with the moisture measuring device.

The object of the present invention is achieved by combining the moisture measuring device with a sensor state monitoring device. The combination of the moisture sensor with a sensor state monitoring device makes it possible to detect error when determining the moisture signal and to display such errors to the driver of the harvesting machine. Furthermore, this combination makes it possible to perform correction measures or calibration. The calibration measures which were previously necessary can be largely dispensed with because the sensor state monitoring device accomplishes a good proportion of the calibration work in an automated fashion. Moreover, the reliability of the moisture measuring device is improved and the driver is relieved of recurring routine work and checks.

In accordance with another aspect of the present invention there is provided a method for determining a moisture value of crop material via a moisture measuring device in an agricultural machine, including the steps of: sensing a moisture value in the crop material via a moisture sensor; transmitting the moisture value to an electronic analyzer; operating the electronic analyzer to offset the moisture value against a calibration-dependent correction value; further processing the offset moisture value for analysis purposes; and determining the correction value at least, in part, as a function of a working state of the machine.

BRIEF DESCRIPTION OF THE DRAWING

The invention is described in more detail below with the aid of the drawing which illustrates a practical example, and wherein.

DETAILED DESCRIPTION

Figure 1:
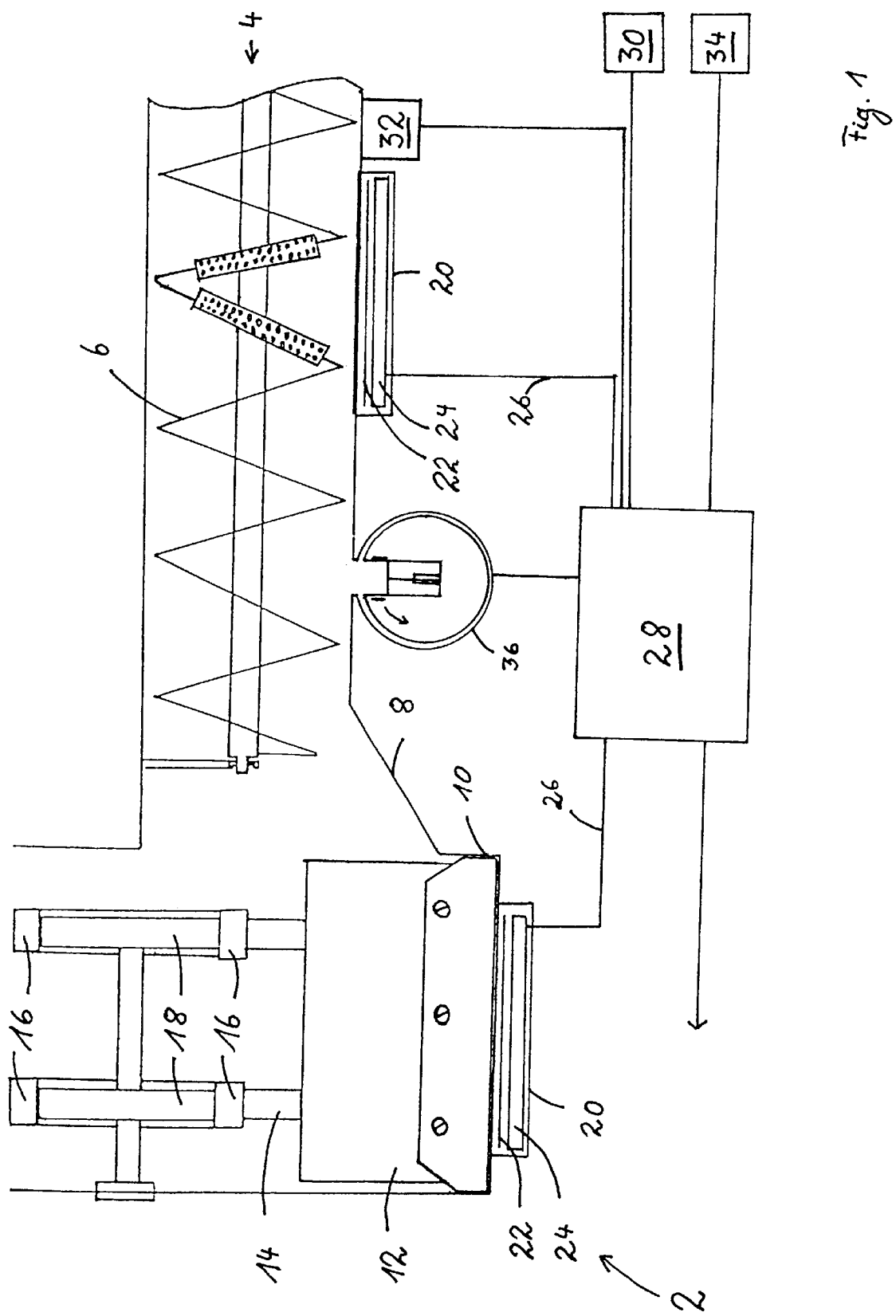
FIG. 1 is a schematic illustration of a grain elevator base and equipped with moisture measuring devices.

FIG. 1 shows a grain elevator base 2 which may be any construction known in the state of the art, which will aid in understanding the manner of operation of an embodiment of the invention to be described. A rotationally driven transverse screw conveyor 4 with screw spirals 6 feeds crop material to the grain elevator base 2. The crop material slides over a ramp 8 into the bottom segment 10, where it is picked up and transported upwards by the elevator paddles 12. The elevator paddles 12 are attached by holding straps 14 to conveyor chains 16 which revolve around sprockets 18.

Moisture sensors 20 are mounted below the transverse screw conveyor 4 and on the lower side of the grain elevator base 2. The moisture sensors 20 are in each case arranged in a housing and determine the moisture of the crop material being conveyed over the sensor surface. The moisture sensors 20 in the practical example consist of an electrode 22 and an electronic device 24 which are connected by wires 26 to the sensor state monitoring device 28. The electronic device 24 transmits the moisture values determined by the moisture sensors 20 to the sensor state monitoring device 28.

The sensor state monitoring device 28 consists of microprocessors and suitable analysis software and can be directly integrated in the electronic device 24, located at another point on the agricultural machine, or located remotely. For description purposes, it is shown here separately. The moisture values can be determined continuously or periodically by the moisture sensors 20 shown in FIG. 1. Operation of the sensor state monitoring device 28 includes correcting the raw moisture values determined by the moisture sensor 20. This is accomplished by processing the values with the sensor state monitoring device 28, using calibration standards. For this purpose, additional sensors 20 transmit their sensor values to the sensor state monitoring device 28. Thus, for example, it is possible to verify the plausibility of the measured moisture values by reference to the values of other sensors. Thus the sensor state monitoring device 28 can detect whether the agricultural machine has switched on the harvesting members at all. Sensor state device 28 can also detect whether the machine is picking up crop material via sensors 30 on a pick-up member such as a cutting mechanism, a treatment member such as a threshing mechanism, a motor, a switching position of a control component, a load measuring device or a speedometer. If the sensor state monitoring device 28 finds, through the sensor values of the sensors 30, that these measurement conditions are not fulfilled, it blocks assignment of the measured moisture value to the crop material or to a quantity of crop material. In the alternative, under the same conditions, the sensor state monitoring device 28 may provide the moisture value with an index which, upon further processing of the moisture value, clarifies that it does not relate to the measurement of crop material. In addition to the analysis of sensor signals which indirectly allow inference of the measurement conditions at the measuring point, the sensor state monitoring device 28 can also receive information from sensors 32 with which the measuring state can be measured directly, such as level or pressure sensors or quality sensors for the crop material which are arranged in the region of the measuring point or at another point of the agricultural machine, such as a harvesting machine. The sensors 32 can signal different measuring states such as, for example:

a) "No material at measuring point", b) "There is an undefined measuring substance at the measuring point", c) "There is a defined measuring substance at the measuring point", d) "There is an additional defined measuring substance at the measuring point", or e) "The measuring substance at the measuring point can cause measuring deviations", f) "The measured material is wheat".

Depending upon these measuring states, the sensor state monitoring device 28 can trigger different correction, display or calibration measures. Thus it is conceivable that the status report a) is needed for diagnostic measuring purposes or calibration measures, b) causes the measured moisture values to be filtered out, for example upon falling below or exceeding the permitted measured quantity, c) signifies normal operation without further correction or calibration measures, d) triggers an amended correction value, e) leads to an amended indication of accuracy, and f) accesses the calibration curves specific to the grain, such as wheat. Instead of or in addition to a correction of the moisture values, single measuring states or all the measuring states determined can be displayed in the cab. The plausibility test can also include a logic test whereby, for example, certain combinations of sensor values are assessed as improbable at a point in time or in a given time interval, and trigger corresponding corrections or actions of the sensor state monitoring device 28. Thus it would be improbable if the measured moisture value in the harvesting machine which is stationary and empty in the measuring region remains unchanged from the moisture value which is determined for subsequently picked-up crop material. A constant moisture value, irrespective of the crop material supplied, leads one to suspect that either the moisture sensor 20 is coated by dirt, which impairs measurement of the current crop material, or there is a defect in the moisture sensor 20. The sensor state monitoring device 28 can then trigger a signal in the cab or initiate subsequent measurement or a check routine for testing the moisture sensor 20. Furthermore, another operability defect occurs when the moisture sensor is mounted at a location where a fluctuating throughput quantity affects the measured moisture value, a sensor 32 indicates fluctuating throughput quantities and the moisture value nevertheless remains constant. In this case the sensor state monitoring device 28 also must trigger a correction and/or display.

In another embodiment of the invention the sensor state monitoring device 28 scans input or memory elements 34 for certain data. Thus, via an input or memory element 34, for example, data on the crop material can be preset to identify the crop material as maize, wheat, barley, etc. There can be additional particulars such as "dry" or "wet" variety, "highly weed-infested", or telemetrically transmitted data on the calibration or plausibility of the moisture values. The driver of the harvesting machine can thus, through input of the harvested material, indirectly calibrate the moisture measuring device for the specific crop material.

An additional moisture measuring device 36 which is connected by a wire to the sensor state monitoring device 28 is also shown in FIG. 1. The additional moisture measuring device 36 consists of a measuring chamber which can be emptied by a movable piston and which is mounted in a rotatably driven housing. After filling the measuring chamber with crop material, the housing rotates in one direction shown by the arrow so that the supply opening to the measuring chamber is closed. During the rotation an associated moisture sensor can determine the moisture value. The material to be measured can be compressed in a particular manner or weighed, and the material to be measured can be measured over a longer time relative to the time for the moisture sensor 20, thus improving the accuracy. The measuring chamber can be equipped with an additional grinding device so that not only the surface moisture, but the moisture of the whole of the crop material can be determined, which also maximizes the accuracy of the determination of the measured value. The moisture measuring device 36 can also use a heating technique, for example infrared drying, in order to measure the quantity of water evaporating. The moisture value of the additional moisture measuring device 36, which is determined as accurately as possible, can then be compared by the sensor state monitoring device 28 as a calibrating value with the moisture value determined by the moisture sensor 20. Furthermore, in case of deviations, a correction factor can be determined.

The method according to the invention provides for determining a correction value which is, at least in part, a function of the working state of the harvesting machine. Working states of the harvesting machine considered may include the fruit-dependent setting, the throughput of material, the speed of conveying, the position of the conveying member or the degree of filling of the measuring chamber or conveying member.

The embodiment described herein, disclosing conveying elements for a combine, can be applied without great effort to other harvesting machines such as forage harvesters, balers, cutter bars, loading trucks and other agricultural machines. Further, the proposed device and method can basically be realized using all known sensor technologies for moisture measurement. It is within the capability of one skilled in the art to make advantageous alterations and additions to the application.

Other objects, features and advantages will be apparent to those skilled in the art. While preferred embodiments and steps of the present invention have been illustrated and described, this has been by way of illustration and the invention should not be limited except as required by the scope of the appended claims.

We claim:

1. An agricultural machine including a moisture measuring device having a first moisture sensor for measuring moisture of a crop material in the machine, a sensor state monitoring device interconnected with the first moisture measuring device for processing and storing measured moisture values, a second moisture sensor for measuring moisture of the crop material over a longer time than the first moisture sensor, means for transmitting the measurements from the second moisture sensor to said sensor state monitoring device, and said sensor state monitoring device being operative for comparing the moisture measurement of the first moisture sensor with those by the second moisture sensor and, in case of a disparity in the values, automatically triggering a correction of the moisture values stored in the sensor state monitoring device by dynamically determining the degree of filling by the crop material.

2. A machine according to claim 1, wherein said sensor state monitoring device is operative to select material-related calibration curves based upon measuring material detected by the sensor mechanism.

3. A machine according to claim 1, wherein said sensor state monitoring device requests input.

4. A machine according to claim 1, including a cab; and wherein a said sensor state monitoring device is arranged for comparing the moisture values of the sensor state monitoring device with those transmitted by the moisture sensor and, in case of a disparity in the values, automatically activates a display in the cab.

5. A machine according to claim 1, wherein said sensor state monitoring device is operative to check certain measuring states and automatically triggers an action as a function of the detected measuring state.

6. A machine according to claim 1, including an electronic device into which said sensor state monitoring device is integrated.

7. A machine according to claim 1, wherein said sensor state monitoring device is operative to select material-related calibration curves based upon measuring material preset by an operator.

8. An agricultural machine including a moisture measuring device having a moisture sensor for measuring moisture of a crop material in the machine, a sensor state monitoring device interconnected with the moisture measuring device for processing and storing measured moisture values, additional sensors for detecting different measuring states of the crop material, means for transmitting the detected measuring states from the additional sensors to said sensor state monitoring device, and said sensor state monitoring device being operative for comparing the moisture measurement of the moisture sensor with the stored moisture values and automatically triggering a correction of the moisture values stored in the sensor state monitoring device by an offset value that is dynamically determined at least, in part, as a function of a working state of the agricultural machine.

9. A method for determining a moisture value of crop material via a moisture measuring device in an agricultural machine, including the steps of: sensing a moisture value in the crop material via a moisture sensor; transmitting the moisture value to an electronic analyzer; operating the electronic analyzer to offset the moisture value against a calibration-dependent correction value; further processing the offset moisture value for analysis purposes; determining the correction value at least, in part, as a function of a working state of the machine; and determining the degree of filling of a measuring chamber and using said degree of filling as the working state.

10. A method for determining a moisture value of crop material via a moisture measuring device in an agricultural machine, including the steps of: sensing a moisture value in the crop material via a moisture sensor; transmitting the moisture value to an electronic analyzer; operating the electronic analyzer to offset the moisture value against a calibration-dependent correction value; further processing the offset moisture value for analysis purposes; determining the correction value at least, in part, as a function of a working state of the machine; and determining the degree of filling of a conveying element of the machine and using the same as the working state.

11. A method for determining a moisture value of crop material via a moisture measuring device in an agricultural machine, including the steps of: sensing a moisture value in the crop material via a moisture sensor; transmitting the moisture value to an electronic analyzer; operating the electronic analyzer to offset the moisture value against a calibration-dependent correction value; further processing the offset moisture value for analysis purposes; and automatically determining the correction value at least, in part, as a function of a working state of the machine, wherein the step of automatically determining the moisture correction value is performed without input from an operator of the agricultural machine by dynamically determining the degree of filling by the crop material.

12. A method according to claim 11, including establishing a grain-dependent setting of the machine and using said setting as the working state.

13. A method according to claim 11, including measuring crop material throughput and using the same as the working state.

14. A method according to claim 11, including determining the conveying speed of at least one conveying element of the machine and using said speed as the working state.

15. A method according to claim 11, including determining the position of a conveying member of the machine and using said determination as the working state.

* * * * *